US010001438B2

(12) United States Patent
Wang et al.

(10) Patent No.: US 10,001,438 B2
(45) Date of Patent: Jun. 19, 2018

(54) METHOD OF SENSING AEROSOL CHARACTERISTIC PARAMETER USING DUAL-WAVELENGTH SCATTERED SIGNAL AND APPLICATION THEREOF

(71) Applicant: Huazhong University of Science and Technology, Wuhan (CN)

(72) Inventors: Shu Wang, Wuhan (CN); Tian Deng, Wuhan (CN); Zheng Dou, Wuhan (CN)

(73) Assignee: Huazhong University of Science and Technology, Wuhan (CN)

( * ) Notice: Subject to any disclaimer, the term of this patent is extended or adjusted under 35 U.S.C. 154(b) by 4 days.

(21) Appl. No.: 15/510,606

(22) PCT Filed: Jun. 23, 2015

(86) PCT No.: PCT/CN2015/082083
§ 371 (c)(1),
(2) Date: Mar. 10, 2017

(87) PCT Pub. No.: WO2016/206000
PCT Pub. Date: Dec. 29, 2016

(65) Prior Publication Data
US 2017/0284934 A1 Oct. 5, 2017

(51) Int. Cl.
*G01N 21/00* (2006.01)
*G01N 21/53* (2006.01)
(52) U.S. Cl.
CPC ................................ *G01N 21/53* (2013.01)

(58) Field of Classification Search
CPC .... G01P 5/001; G01N 21/49; G01N 15/0205; G01N 2021/513; G01N 21/53;
(Continued)

(56) References Cited

U.S. PATENT DOCUMENTS 8,047,055 B2 * 11/2011 Wang ................. G01N 15/0205
250/287
8,941,505 B2 * 1/2015 Dohi ...................... G01N 21/53
250/573
(Continued)

*Primary Examiner* — Hoa Pham
(74) *Attorney, Agent, or Firm* — Wang Law Firm, Inc.

(57) ABSTRACT

The present invention relates to a method of sensing aerosol characteristic parameters using dual-wavelength light scattered signals and the application thereof, and belongs to the technical field of fire warning. The method procedures include measuring the scattered light power of two different wavelengths, calculating the surface area concentration and the volume concentration of aerosol, and obtaining the Sauter mean diameter of the aerosol the surface area concentration, the volume concentration and the aerosol Sauter mean diameter are compared with corresponding thresholds, and then corresponding fire alarm signals are emitted. By the adoption of the method, on one hand, the particle size of an aerosol can be judged according to the Sauter mean diameter, so that whether a fire really occurs can be identified in time and a fire alarm signal or a non-fire factor interference prompt signal can be emitted timely and correctly; and on the other hand, the characteristic parameters of the aerosol can be obtained by the surface area concentration and the volume concentration of the aerosol, so that a fire type alarm signal can be judged and emitted to allow targeted and rational measures to be taken.

4 Claims, 8 Drawing Sheets

Figure 1:
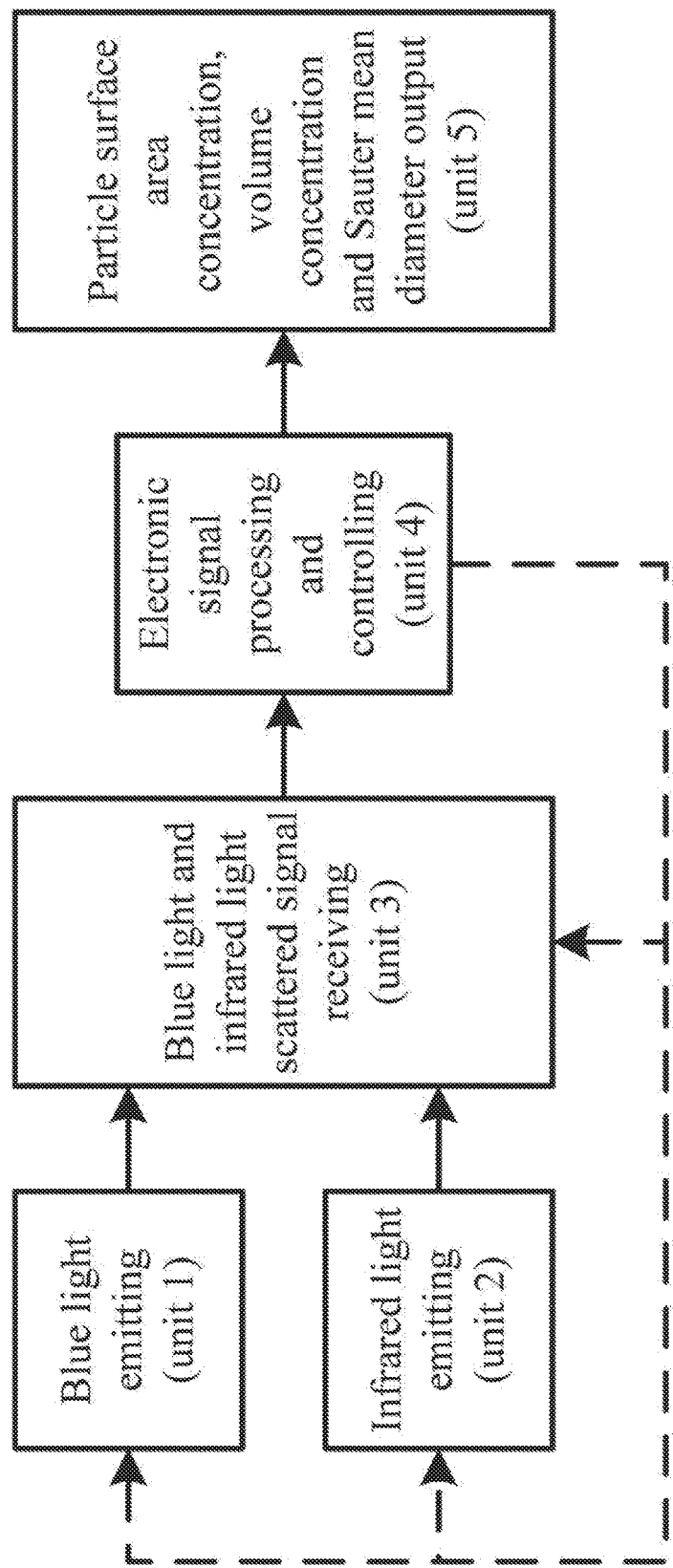

(58) Field of Classification Search
CPC ...... G08B 29/18; G08B 17/107; G08B 17/12; G08B 17/125; G08B 17/103; G08B 17/11
USPC .................. 356/432–440, 318, 73, 335–343; 250/573; 340/630, 628
See application file for complete search history.

(56) References Cited

U.S. PATENT DOCUMENTS

| | | | |
|---|---|---|---|
| 9,377,481 B1* | 6/2016 | Greenberg | G01P 5/001 |
| 2013/0016339 A1* | 1/2013 | Edwards | C09D 7/41 356/51 |

* cited by examiner

METHOD OF SENSING AEROSOL CHARACTERISTIC PARAMETER USING DUAL-WAVELENGTH SCATTERED SIGNAL AND APPLICATION THEREOF

TECHNICAL FIELD

The present invention relates to a method of detecting and sensing an aerosol, and in particular to a method of sensing surface area concentration, volume (mass) concentration and Sauter particle size of an aerosol using dual-wavelength light scattered signals, as well as the application of the method to fire smoke detection, and belongs to the technical field of fire warning.

BACKGROUND ART

The smoke fire detection technique based on the light scattering principle of an aerosol has been widely applied since 1970s when the technique was first used. However, the surface area and particle size of an aerosol cannot be sensed or fire smoke cannot be distinguished from dust and steam in the prior art, and therefore false alarm becomes the biggest factor affecting detection effectiveness.

In general, the particle size of a fire aerosol generated from material burning is smaller than 1 μm, and the particle size of a non-fire aerosol such as steam and dust is larger than 1 μm. For the same mass concentration, a small-size aerosol is more in particle number and large in surface area, a large-size aerosol is less in particle number and small in surface area, and therefore a fire aerosol and a non-fire aerosol can be distinguished more effectively based on the surface area concentration of the aerosol and other characteristic parameters such as mass (volume) concentration and Sauter diameter of the aerosol all together.

Chinese patents with the patent No. 200410031104.5, the patent No. 200980138873.6 and the patent No. 201180039383.8 all disclose methods of distinguishing aerosol particles with diameter larger than 1 μm and smaller than 1 μm by using scattered light signals with two different wavelengths, so as to reduce the false alarm rate of a fire smoke alarm. However, the specific particle size value and surface area concentration cannot be sensed by using these methods. A Chinese patent application with the application No. 201410748629.4 discloses a method of sensing the median particle size of an aerosol using scattered light signals with two different wavelengths, but the method cannot sense the surface area concentration of an aerosol. The document "Greenberg, P. S. and Fischer, D. G., Advanced Particulate Sensors for Spacecraft Early Warning Fire Detection, Paper No. AIAA2010-6243, 40th International Conference on Environmental Systems, Barcelona, Spain, Jul. 11-15, 2010" provides a method of measuring the surface area concentration and the mass concentration of an aerosol using a specific optical structure working at the same wavelength and different scattering angles. However, according to the aerosol Mie scattering principle, balanced response of large and small particles can hardly be achieved with the same wavelength, and the measurement error of the method is large.

To overcome the defects in the prior art, a Chinese patent application with the application No. 201410748629.4 provides a method of sensing a particle size of an aerosol using dual-wavelength light scattered signals capable of identifying different types of fires and steam and dust interference according to a median particle size value and giving alarms with corresponding alarm signals. The method comprises the steps of calculating the ratio R of scattered light power of blue light to scattered light power of infrared light after receiving corresponding scattered signals of the aerosol, expressed by the scattered light power $P_{BL}$ of blue light and the scattered light power $P_{IR}$ of infrared light; determining a median particle size $d_{med}$ according to the relationship between the ratio R of scattered light power of blue light to scattered light power of infrared light and the median particle size $d_{med}$ of the aerosol; and comparing the scattered light power $P_{BL}$ of blue light and the scattered light power $P_{IR}$ of infrared light with corresponding set thresholds $P_{BLth}$ and $P_{IRth}$ and emitting corresponding interference prompt signals or corresponding fire alarm signals. Though the method can be used for judging and emitting fire type alarm signals so that targeted and rational measures can be taken and a non-fire aerosol false alarm can be avoided to a certain extent, the median particle size of the aerosol cannot be obtained directly due to the fact that the ratio R has no corresponding physical meaning; and it is required that an experiment be conducted on R in advance so as to obtain a particle size spectrum curve covering all particle sizes from small to large and store the particle size spectrum curve, and only through comparison and search can the particle size be obtained, which is both inconvenient and inaccurate. Specifically, it can be learned from a curve of a non-linear relationship between R and the median particle size of the aerosol, for particle sizes smaller than 200 nm and larger than 1,000 nm, the ratio is in a non-linear area, making it difficult to obtain an accurate result, and for particle sizes larger than 1,500 nm, distinguishing fails due to the fact that the ratio R changes too slightly. Besides, as the surface area concentration of the aerosol cannot be obtained with the method, the small-particle size fire aerosol with large surface area concentration but small mass (volume) concentration cannot be effectively sensed. Furthermore, the characteristic parameters of the aerosol are represented by amount concentration, surface area concentration, mass (volume) concentration and particle size distribution, and the larger the number of sensed characteristic parameters is, the more accurate the judgment tends to be.

SUMMARY OF THE INVENTION

The present invention aims to provide a method of sensing three characteristic parameters, including surface area concentration, volume concentration and Sauter mean diameter, of an aerosol using dual-wavelength light scattered signals in view of the defects of the above-mentioned technique, so that different types of fire smoke and steam and dust interference can be identified according to the parameters and alarms can be given with different alarm signals, the capacity of identifying and judging aerosols with various particle sizes is improved effectively, and then the precision of fire alarms is improved remarkably.

Researches show that there are various characteristic parameters of an aerosol, wherein surface area concentration, volume concentration (if matter density is known, mass concentration can be obtained) and Sauter mean diameter are the most important parameters, which not only measure the characteristics of an aerosol, but also reflect a particle distribution condition, and therefore fire smoke can be judged more effectively and accurately by sensing these parameters.

Theoretically, quantitative distribution of particle sizes of aerosols generated from material burning can be described with a log-normal distribution function, particle size distribution standard deviation is approximately 1.6-1.9, changes are small, and the general particle size is smaller than 1 μm.

Figure 8:
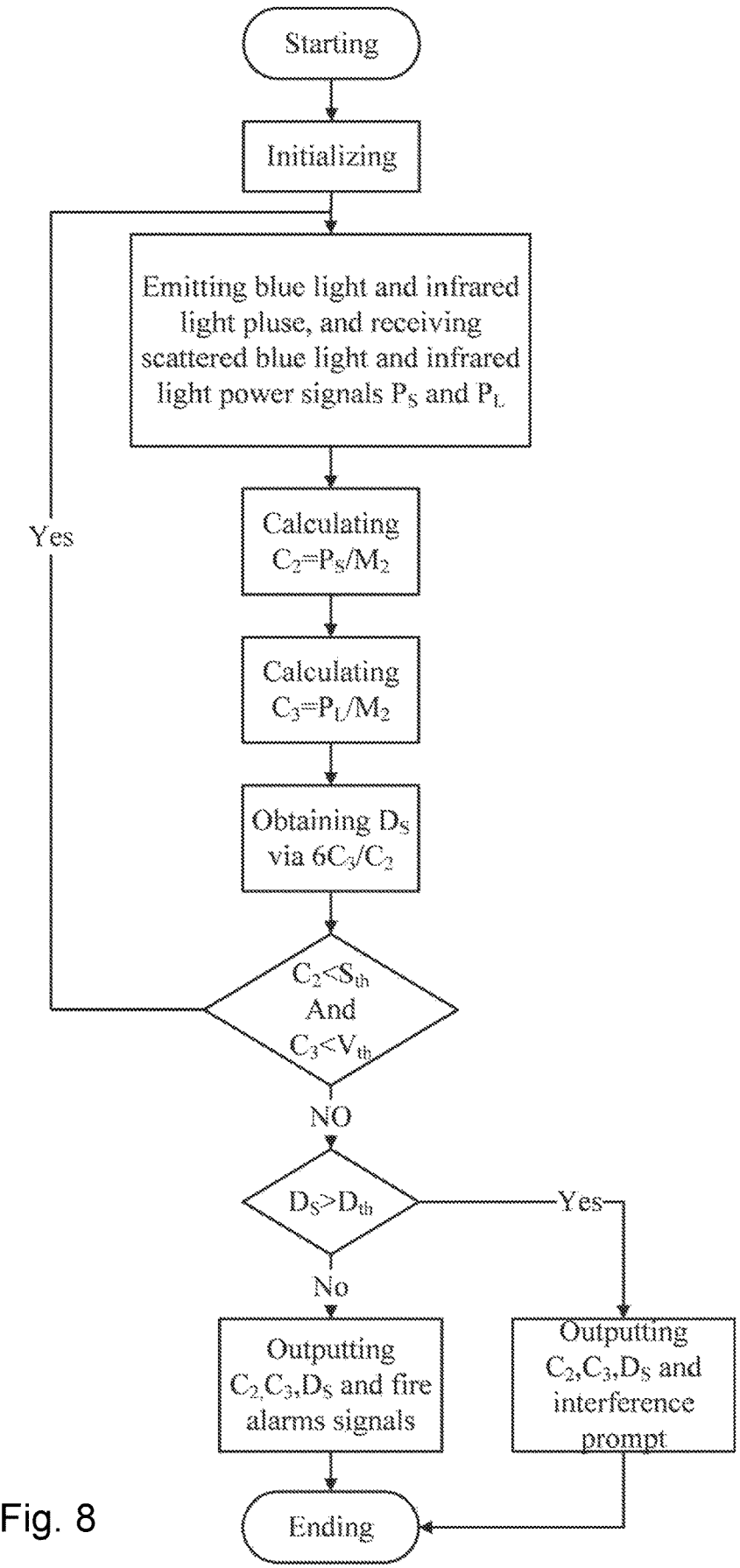

The applicant finds through research and analysis that when the particle size of an aerosol complies with lognormal distribution and distribution standard deviation is within a certain range, for incident light with shorter wavelength, particle light scattered power directly corresponds to the surface area concentration of the aerosol at a certain scattering angle (it is generally required that the included angle between the optical axis of a light emitting device and the optical axis of a light receiving device be larger than 90°), deviation is small, and the numerical value of the surface area concentration of aerosol can be obtained accordingly and serve as an aerosol surface area concentration output signal of a sensor; for incident light with longer wavelength, particle light scattered power directly corresponds to the volume concentration of the aerosol at a certain scattering angle (it is generally required that the included angle between the optical axis of a light emitting device and the optical axis of a light receiving device be smaller than 90°), deviation is small, and the numerical value of the volume concentration of the aerosol can be obtained accordingly and serve as an aerosol volume concentration output signal of a sensor. By definition, the ratio of volume concentration to surface area concentration is in direct proportion to the Sauter mean diameter of the aerosol.

Therefore, according to received particle light scattered power, the Sauter mean diameter of the aerosol can be obtained by the corresponding proportional relationship by calculating volume concentration and surface area concentration, then different types of fires and steam and dust interference can be identified, and alarms can be given with different alarm signals, so that targeted and rational fire-fighting measures can be taken.

The method of sensing aerosol characteristic parameters using dual-wavelength light scattered signals of the present invention comprises the following steps:

step 1, constructing a detector consisting of light emitting devices with shorter and longer wavelengths respectively, and two channels of detection signals, wherein an included angle between the optical axis of the first channel of light emitting device with shorter wavelength and the optical axis of a light receiving device is larger than 90°, and an included angle between the optical axis of the second channel of light emitting device with longer wavelength and the optical axis of the light receiving device is smaller than 90°;

step 2, for received scattered signal of aerosol by the first channel (shorter wavelength), expressed by shorter-wavelength light scattered light power $P_S$, calculating the corresponding surface area concentration $C_2$ of the aerosol via the formula below:

$$C_2 = \frac{P_S}{M_2}$$

wherein the unit of $C_2$ is $nm^2/cm^3$, the unit of $P_S$ is voltage V converted from scattered light power generally (can also be a quantitative value of conversion voltage), $M_2$ is a scattered light surface area concentration conversion coefficient which is a constant corresponding to a given optical structure and electric parameters, $M_2$ is generally $(1.5\text{-}3.5)\times 10^{-10}$, the unit of $M_2$ is $(nm^2/cm^3)^{-1}$ when light power is a quantitative value and is $V/(nm^2/cm^3)$ when light power is expressed by voltage, and $M_2$ can be calibrated using measurement equipment such as a particle sizer;

step 3, for received scattered signal of aerosol by the second channel (longer wavelength), expressed by longer-wavelength light scattered light power $P_L$, calculating the volume concentration $C_3$ (if matter density is known, mass concentration can be obtained using volume concentration) of the aerosol via the formula below:

$$C_3 = \frac{P_L}{M_3}$$

wherein the unit of $C_3$ is $nm^3/cm^3$ (or if matter density is known, the unit of mass concentration is $\mu g/m^3$), the unit of $P_L$ is light power conversion voltage V (can also be a quantitative value of conversion voltage), $M_3$ is a scattered light volume (or mass) concentration conversion coefficient which is a constant corresponding to a given optical structure and electric parameters, the numerical range of $M_3$ is generally $(0.5\text{-}2.5)\times 10^{-12}$ when $M_3$ is a volume concentration conversion coefficient, the unit of $M_3$ is $(nm^3/cm^3)^{-1}$ when light power is a quantitative value and is $V/(nm^3/cm^3)$ when light power is expressed by voltage V, mass concentration can be obtained if matter density is known, the numerical range of $M_3$ is generally $(0.5\text{-}2.5)\times 10^{-3}$ and the unit is $(\mu g/m^3)^{-1}$ when $M_3$ is a mass concentration conversion coefficient, and $M_3$ can be calibrated using measurement equipment such as a particle sizer;

step 4, calculating the ratio of the volume concentration $C_3$ (volume concentration is adopted herein, if mass concentration is adopted in previous steps, volume concentration can be obtained by dividing mass concentration by density) of the aerosol to the surface area concentration $C_2$ of the aerosol via the formula below, so as to obtain the Sauter mean diameter $D_S$ of the aerosol, of which the unit is nm:

$$D_S = 6\frac{C_3}{C_2},$$

and step 5, directly outputting the three parameters, including the volume concentration $C_3$, the surface area concentration $C_2$ and the Sauter diameter $D_S$, of the aerosol as aerosol characteristics, and simultaneously comparing the three parameters with corresponding set thresholds $V_{th}$, $S_{th}$ and $D_{th}$:

returning to step 1 when the volume concentration $C_3$ and the surface area concentration $C_2$ are lower than the corresponding preset thresholds $V_{th}$ and $S_{th}$ respectively; and judging whether the particle Sauter mean diameter $D_S$ is larger than the set threshold $D_{th}$ when at least one of the volume concentration $C_3$ and the surface area concentration $C_2$ is higher than the corresponding preset threshold $V_{th}$ or $S_{th}$; if so, emitting a corresponding non-fire factor interference prompt signal; and if not, emitting a corresponding fire alarm signal.

More specifically, in step 5, if the corresponding interference prompt signal is emitted when only the volume concentration $C_3$ is larger than the preset threshold $V_{th}$, the Sauter diameter of dust or a steam aerosol can be prompted according to the value of $D_S$. In this case, the larger $C_3$ is, the larger the Sauter diameter is, the value of the Sauter diameter $D_S$ and the numerical values of the surface area concentration $C_2$ and the volume concentration $C_3$ are output, and a prompt of macroparticle high-volume concentration non-fire factor (such as dust or steam) interference is given; if the surface area concentration $C_2$ and the volume concentration $C_3$ are both larger than the corresponding preset thresholds $S_{th}$ and $V_{th}$, it can be learned from the Sauter diameter calculation formula in step 4 that the particle size of the aerosol at the moment exceeds $D_{th}$ but cannot be very large, at the moment, the Sauter diameter depends on the specific ratio of the volume concentration to the surface area concentration, and accordingly, the value of the Sauter diameter $D_S$ and the numerical values of the surface area concentration $C_2$ and the volume concentration $C_3$ are output, and a prompt of high-surface area concentration and high-volume concentration dust or steam interference is given.

Further, in step 5, when the corresponding fire alarm signal is emitted, the Sauter mean diameter of a fire aerosol can be prompted according to the value of $D_S$; when $D_S$ is smaller than a preset division value $D_{div}$ for distinguishing large-particle size fire smoke from small-particle size fire smoke, it can be learned from the Sauter diameter calculation formula in step 4 that at the moment, only the surface area concentration $C_2$ is larger than the corresponding preset threshold $S_{th}$ usually, the larger the surface area concentration is, the smaller the Sauter diameter tends to be, in this case, the value of the Sauter diameter $D_S$ and the numerical values of the surface area concentration $C_2$ and the volume concentration $C_3$ are output, and an alarm of fire smoke aerosol with high surface area concentration is given (the larger the surface area concentration is, the more serious damage to the lung of people tends to be); and when the volume concentration $C_3$ and the surface area concentration $C_2$ are both larger than the corresponding preset thresholds $V_{th}$ and $S_{th}$, at the moment, the Sauter diameter depends on the specific ratio of the volume concentration to the surface area concentration, generally $D_S$ is between the division value $D_{div}$ for distinguishing values of fire smoke particle sizes and $D_{th}$, in this case, the value of the Sauter diameter $D_S$ and the numerical values of the surface area concentration $C_2$ and the volume concentration $C_3$ are output, and an alarm of a large-particle size fire smoke aerosol with high surface area concentration and high volume concentration is given.

Due to the fact that the surface area concentration, the volume concentration and the Sauter mean diameter of the aerosol are directly measured, search of a particle size spectrum curve or table covering all particle sizes from small to large obtained through an experiment conducted in advance is not needed any more, and therefore the particle size can be judged more directly and accurately. Specifically, a non-linear relationship is formed between the optical signal ratio and the particle size according to the closest prior art, for particle sizes smaller than 200 nm and larger than 1,000 nm, the ratio R is in a non-linear area, making it difficult to obtain an accurate result, and for particle sizes larger than 1,500 nm, distinguishing fails due to the fact that the ratio R changes too slightly. According the present invention, a linear relationship is formed between Sauter diameter and the ratio of volume concentration to surface area concentration, and a result can still be obtained when the particle size is smaller than 200 nm or larger than 1,000 nm. Besides, the physical meaning of the surface area concentration and the volume concentration of the aerosol is quite clear, and direct output of surface area concentration and volume concentration facilitates the determination of fire and non-fire interference aerosols; more specifically, if only the surface area concentration exceeds the corresponding threshold, the Sauter particle size is small, and small-particle size fire smoke with high surface area concentration is output, and when volume concentration does not exceed the corresponding threshold, according to the Sauter diameter formula in step 4, the larger the surface area concentration is, the smaller the particle size tends to be, and then fire hazard is more serious. An aerosol with large particle size is obtained through Sauter diameter; if only volume concentration exceeds the preset threshold, a result shows a large-particle size non-fire interference aerosol; and when surface area concentration does not exceed the threshold, according to the Sauter diameter formula in step 4, the larger the volume concentration is, the larger the particle size tends to be, and then the result of large-particle size dust or steam non-fire interference particles with high volume concentration is more definite. Therefore, by the adoption of the present invention, on one hand, the particle size of an aerosol can be judged according to Sauter mean diameter, so that whether a fire really occurs can be identified in time and a fire alarm signal or a non-fire factor interference prompt signal can be emitted timely and correctly; and on the other hand, the characteristic parameters of the aerosol can be obtained by the volume concentration and the surface area concentration of the aerosol, so that a fire type alarm signal can be judged and emitted to allow targeted and rational measures to be taken.

Besides, due to the fact that the surface area concentration, the volume or mass concentration and the Sauter mean diameter of the aerosol are directly sensed using the method of the present invention, the method can also be used as a sensor to be applied to occasions where the characteristic parameters of an aerosol need to be measured in environment monitoring, industrial production and daily life.

BRIEF DESCRIPTION OF THE DRAWINGS

The present invention will further be described with reference to the accompanying drawings.

FIG. 1 is a system schematic diagram of an embodiment of the present invention.

FIG. 2 is a diagram of an optical configuration of an embodiment of the present invention.

FIG. 3 is a schematic circuit diagram of an embodiment of the present invention.

FIG. 4 is an aerosol surface area concentration measurement result of an embodiment of the present invention, showing the relationship between the surface area concentration of Di-Ethyl-Hexyl-Sebacat (DEHS) aerosol with standard deviation of 1.16-1.24 and different peak particle sizes ranging from 259 nm to 1,181 nm and surface area concentration measured with a scanning mobility particle sizer.

FIG. 5 is an aerosol volume concentration measurement result of an embodiment of the present invention, showing the relationship between the volume concentration of DEHS aerosol with standard deviation of 1.16-1.24 and different peak particle sizes ranging from 259 nm to 1,181 nm and volume concentration measured with a scanning mobility particle sizer.

FIG. 6 is an aerosol Sauter mean diameter measurement result of an embodiment of the present invention, showing the relationship between the Sauter mean diameter of DEHS aerosol with standard deviation of 1.16-1.24 and different peak particle sizes ranging from 259 nm to 1,181 nm and peak particle size measured with a scanning mobility particle sizer.

FIG. 7 is a linear relationship between the ratio of volume concentration to surface area concentration and Sauter particle size of an embodiment of the present invention.

FIG. 8 is a flow diagram of an embodiment of the present invention.

DETAILED DESCRIPTION OF THE INVENTION

Embodiment 1

According to the present embodiment, a method of sensing aerosol characteristic parameters using dual-wavelength light scattered signals is applied to a fire smoke detection system as shown in FIG. 1. The system has two emission devices 1 and 2 with shorter wavelength (blue light) and longer wavelength (infrared light) respectively, a receiving device 3 of blue light and infrared light scattered light power, an electronic signal processing and controlling unit 4, and a particle surface area concentration, volume concentration and Sauter mean diameter output unit 5. An ultraviolet light or blue light source with wavelength of 280-490 nm is adopted to emit blue light, and an infrared light source with wavelength of 830-1,050 nm is adopted to emit infrared light.

Figure 2:
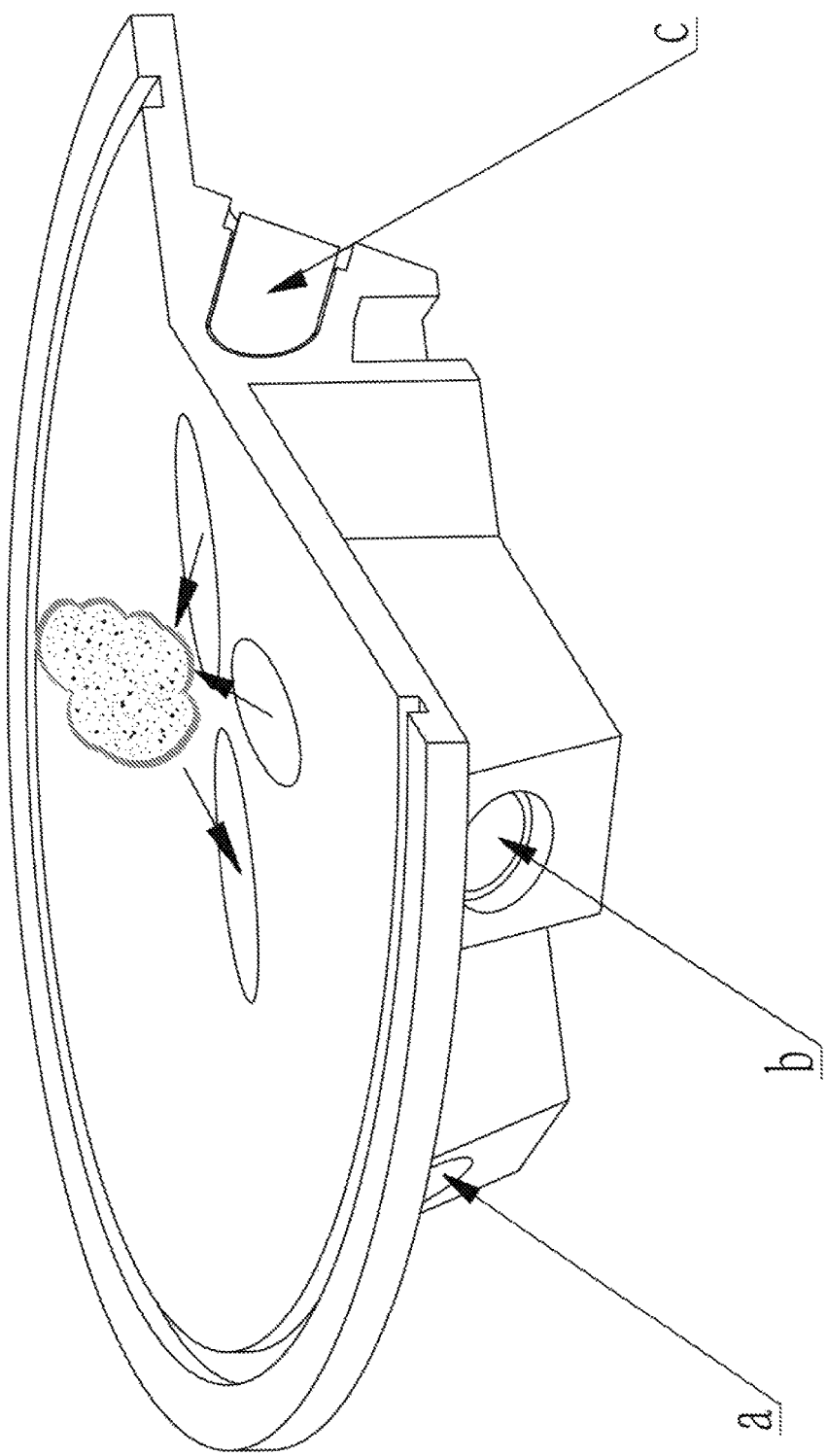
Figure 3:
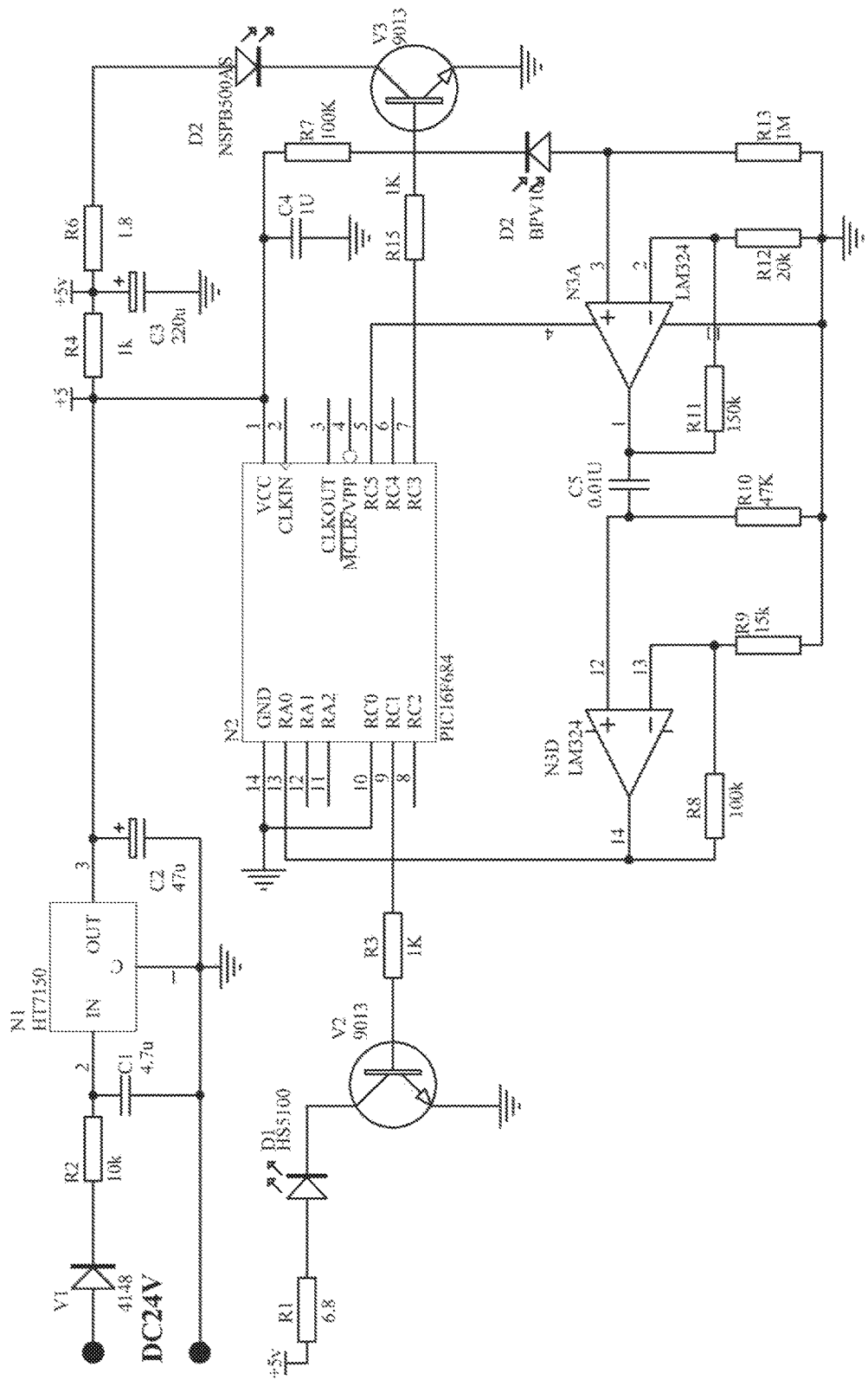

The diagram of an optical configuration of the present embodiment is shown in FIG. 2, wherein a is a blue light and infrared light receiving diode, b is an infrared light emitting diode, and c is a blue light emitting diode. The electronic signal processing and controlling unit 4 comprises a processing and controlling circuit containing a CPU, and the exemplary configuration thereof is shown in FIG. 3, wherein $D_1$ is an infrared light emitting diode, $D_2$ is a blue light emitting diode, $D_3$ is a blue light and infrared light receiving diode, $N_1$ is a power circuit element, $N_2$ is an electronic signal processing, transmitting and controlling unit containing a CPU, signal processing is achieved in $N_2$, an $RC_2$ port of $N_2$ serves as output of signal transmission, and $N_3$ is a received light signal amplifying circuit element.

According to the system in the present embodiment, an aerosol surface area concentration conversion coefficient $M_2$ and volume concentration conversion coefficient $M_3$ can be obtained through experimental calibration. The detailed process is that Di-Ethyl-Hexyl-Sebacat (DEHS) aerosol with standard deviation of 1.24, Sauter particle size of 472.3 nm, surface area concentration of $1.41 \times 10^{11}$ ($nm^2/cm^3$), and mass concentration of $1.01 \times 10^4$ $\mu g/m^3$ (volume concentration of $1.11 \times 10^{13}$ ($nm^3/cm^3$)) is introduced into a detector, a blue light signal quantitative value is measured to be 41# (blue light output on which corresponding light power acts is 41/256×5V=0.8V), and the surface area concentration conversion coefficient $M_2$ of the present embodiment is calculated to be $2.91 \times 10^{-10}$ (#/($nm^2/cm^3$)). Meanwhile, an infrared light signal quantitative value is measured to be 12# (infrared light output on which corresponding light power acts is 12/256×5V=0.23V), and the mass concentration conversion coefficient $M_3$ is calculated to be $1.19 \times 10^{-3}$ (#/($\mu g/m^3$)), or the volume concentration conversion coefficient $M_3$ is calculated to be $1.08 \times 10^{-12}$ (#/($nm^3/cm^3$)).

Figure 4:
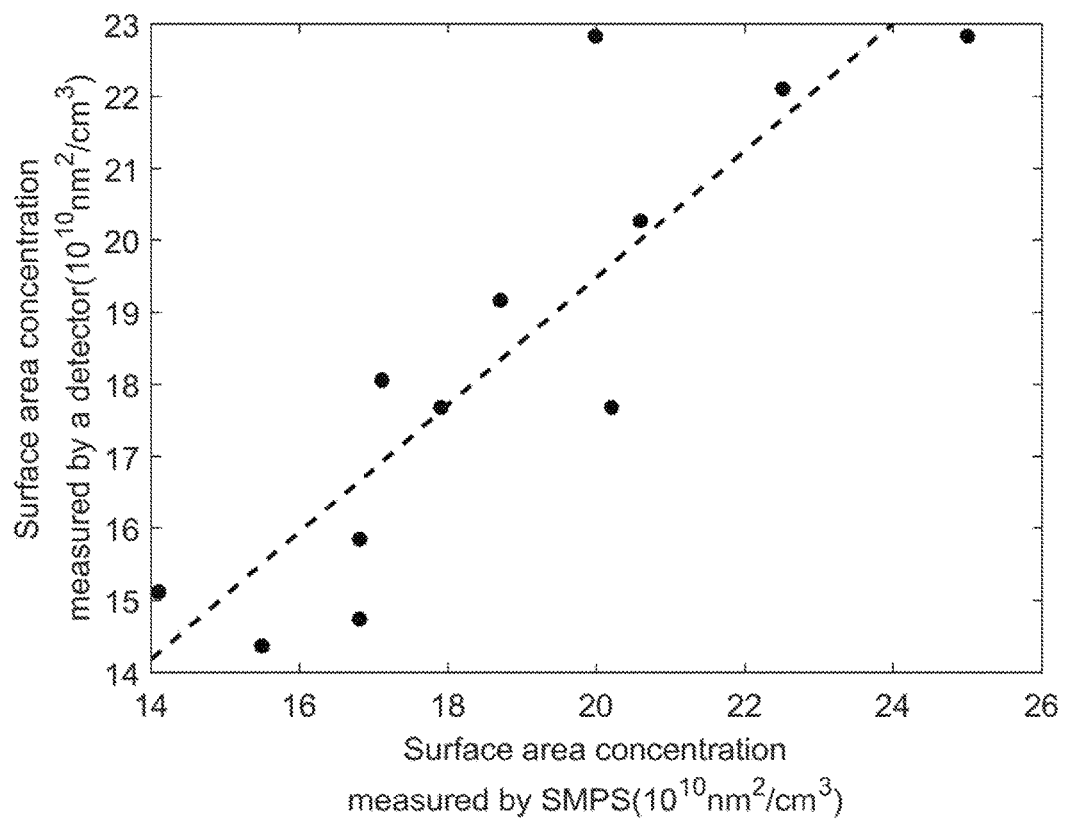
Figure 5:
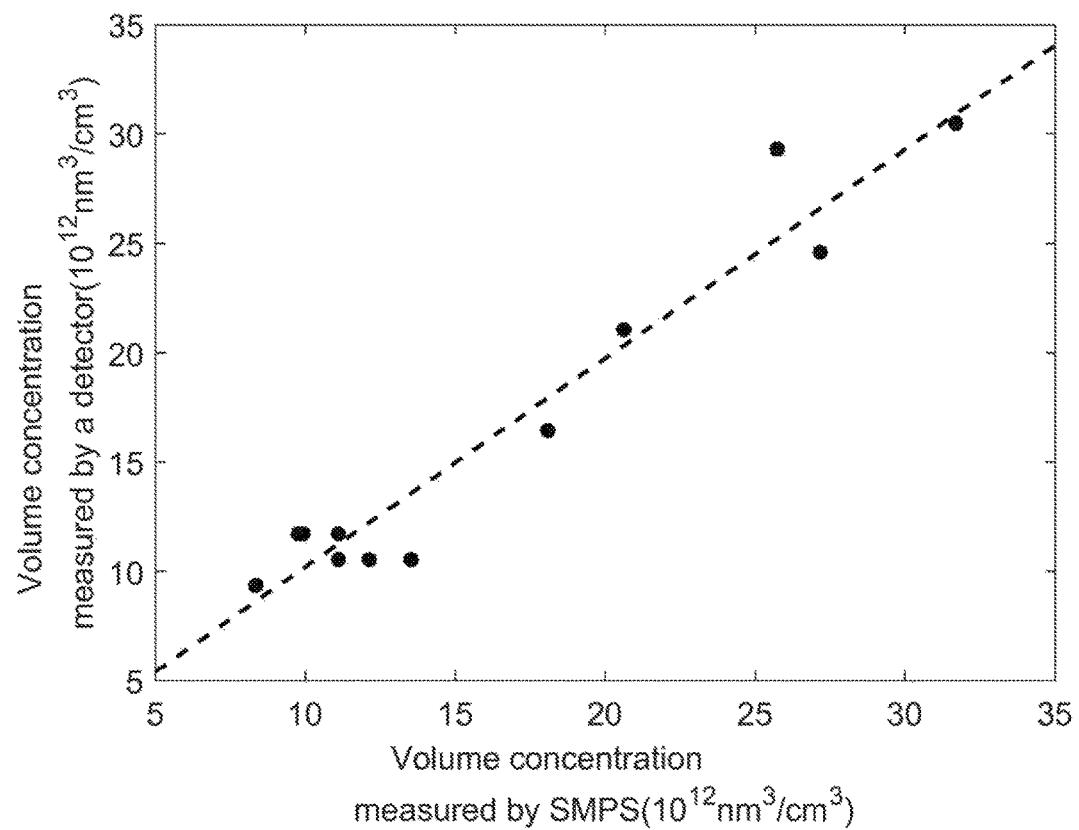
Figure 6:
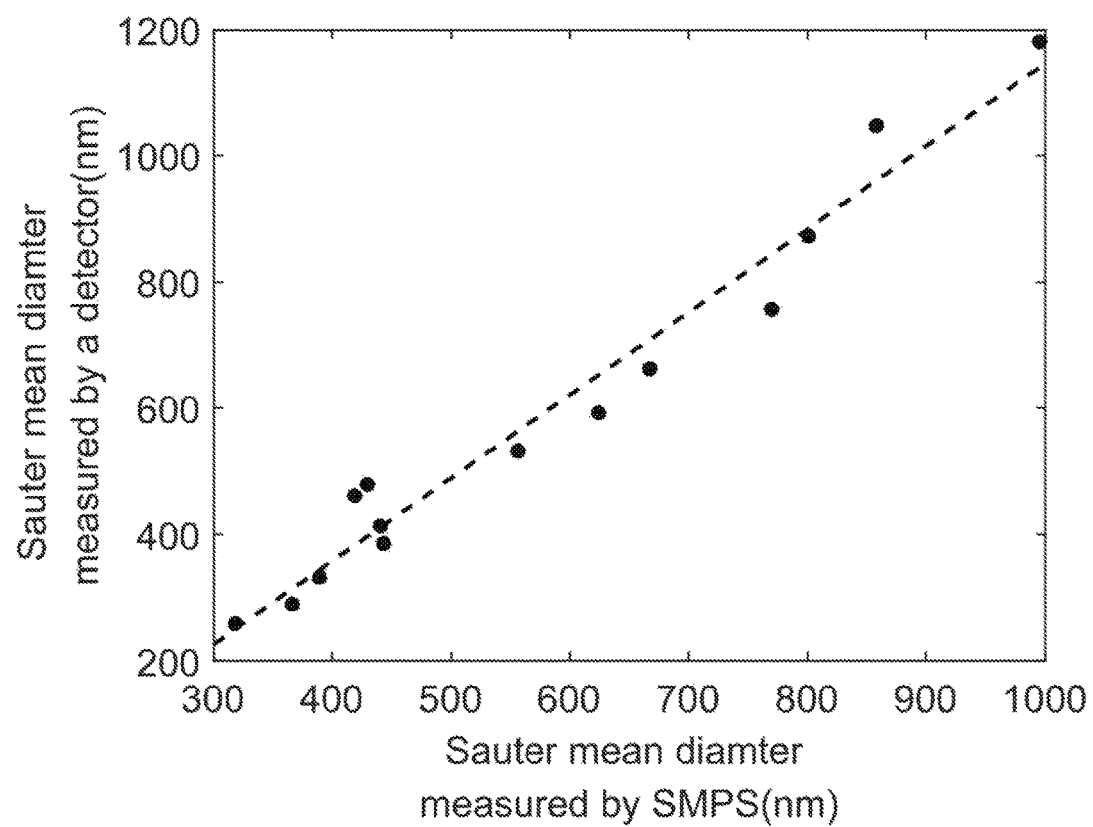

To verify the accuracy of the calibration above, the DEHS aerosol with standard deviation of 1.16-1.24 and different peak particle sizes ranging from 259 nm to 1,181 nm is measured by means of the system in the present embodiment, meanwhile, a scanning mobility particle sizer (SMPS) is adopted as a measurement contrast, and then an aerosol surface area concentration measurement result as shown in FIG. 4, an aerosol volume concentration measurement result as shown in FIG. 5 and an aerosol Sauter mean diameter measurement result as shown in FIG. 6 are obtained.

The specific implementation of the present embodiment to fire detection comprises the steps (see FIG. 8):

step 1, constructing a detector consisting of light emitting devices with shorter and longer wavelengths respectively, and two channels of detection signals, wherein an included angle between the optical axis of the first channel of light emitting device and the optical axis of a light receiving device is larger than 90° (120° in the present embodiment), and an included angle between the optical axis of the second channel of light emitting device and the optical axis of the light receiving device is smaller than 90° (85° in the present embodiment);

step 2, after a scattered signal of aerosol expressed by shorter-wavelength light scattered light power $P_S$ is received by the first channel, calculating the surface area concentration $C_2$ of aerosol via the formula below:

$$C_2 = \frac{P_S}{M_2}$$

FIG. 4 shows the relationship between the surface area concentration of the DEHS aerosol with standard deviation of 1.16-1.24 and different peak particle sizes ranging from 259 nm to 1,181 nm and surface area concentration measured with a scanning mobility particle sizer, by means of which it is not difficult to determine the scattered light surface area concentration conversion coefficient $M_2$;

step 3, after a scattered signal of aerosol expressed by longer-wavelength light scattered light power $P_L$ is received by the second channel, calculating the volume concentration $C_3$ (if matter density is known, mass concentration can be obtained) of aerosol via the formula below:

$$C_3 = \frac{P_L}{M_3}$$

FIG. 5 shows the relationship between the volume concentration of the DEHS aerosol with standard deviation of 1.16-1.24 and different peak particle sizes ranging from 259 nm to 1,181 nm and volume concentration measured with a scanning mobility particle sizer, by means of which it is not difficult to determine the scattered light volume concentration conversion coefficient $M_3$;

step 4, calculating the ratio of the volume concentration $C_3$ of the aerosol to the surface area concentration $C_2$ of the aerosol, so as to obtain the Sauter mean diameter $D_S$ of the aerosol:

$$D_S = 6\frac{C_3}{C_2}$$

FIG. 6 shows the relationship between the Sauter mean diameter of the DEHS aerosol with standard deviation of 1.16-1.24 and different peak particle sizes ranging from 259 nm to 1,181 nm and peak particle size measured with a scanning mobility particle sizer; and step 5, comparing the volume concentration $C_3$ of the aerosol and the surface area concentration $C_2$ of the aerosol with corresponding set thresholds $V_{th}$ and $S_{th}$, and processing various possibilities as follows:

(1) returning to step 1 when the volume concentration $C_3$ and the surface area concentration $C_2$ are lower than the corresponding preset thresholds $V_{th}$ and $S_{th}$ respectively; and (2) judging whether the Sauter mean diameter $D_S$ is larger than the set threshold $D_{th}$ when at least one of the volume concentration $C_3$ and the surface area concentration $C_2$ is higher than the corresponding preset threshold $V_{th}$ or $S_{th}$, wherein $D_{th}$ is set to be 1 µm in the present embodiment ($D_{th}$ is usually 0.9-1.1 µm and can be set according to using environments):

if so, emitting a corresponding interference prompt signal, wherein there are two situations here: if only the volume concentration $C_3$ is larger than the corresponding preset threshold $V_{th}$, the value of the Sauter diameter $D_S$ and the numerical values of the surface area concentration $C_2$ and the volume concentration $C_3$ are output, and an alarm of large-particle high-volume concentration dust or steam interference is given; and if the surface area concentration $C_2$ and the volume concentration $C_3$ are both larger than the corresponding preset thresholds $S_{th}$ and $V_{th}$, the value of the Sauter diameter $D_S$ and the numerical values of the surface area concentration $C_2$ and the volume concentration $C_3$ are output, and an alarm of high-surface area concentration and high-volume concentration dust or steam interference is given; and if not, emitting a corresponding fire alarm signal, wherein there are two situations here: if only the surface area concentration $C_2$ is larger than the corresponding preset threshold $S_{th}$ and Sauter mean diameter $D_S$ is smaller than a preset division value $D_{div}$ (0.5 µm in the present embodiment) for distinguishing large-particle size fire smoke from small-particle size fire smoke, the value of the Sauter diameter $D_S$ and the numerical values of the surface area concentration $C_2$ and the volume concentration $C_3$ are output, and an alarm of a small-particle size fire smoke aerosol with high surface area concentration is given; and if the surface area concentration $C_2$ and the volume concentration $C_3$ are both larger than the corresponding preset thresholds $V_{th}$ and $S_{th}$ and the Sauter mean diameter $D_S$ is between 0.5 µm and $D_{th}$, the value of the Sauter diameter $D_S$ and the numerical values of the surface area concentration $C_2$ and the volume concentration $C_3$ are output, and an alarm of a large-particle size fire smoke aerosol with high surface area concentration and high volume concentration is given.

Figure 7:
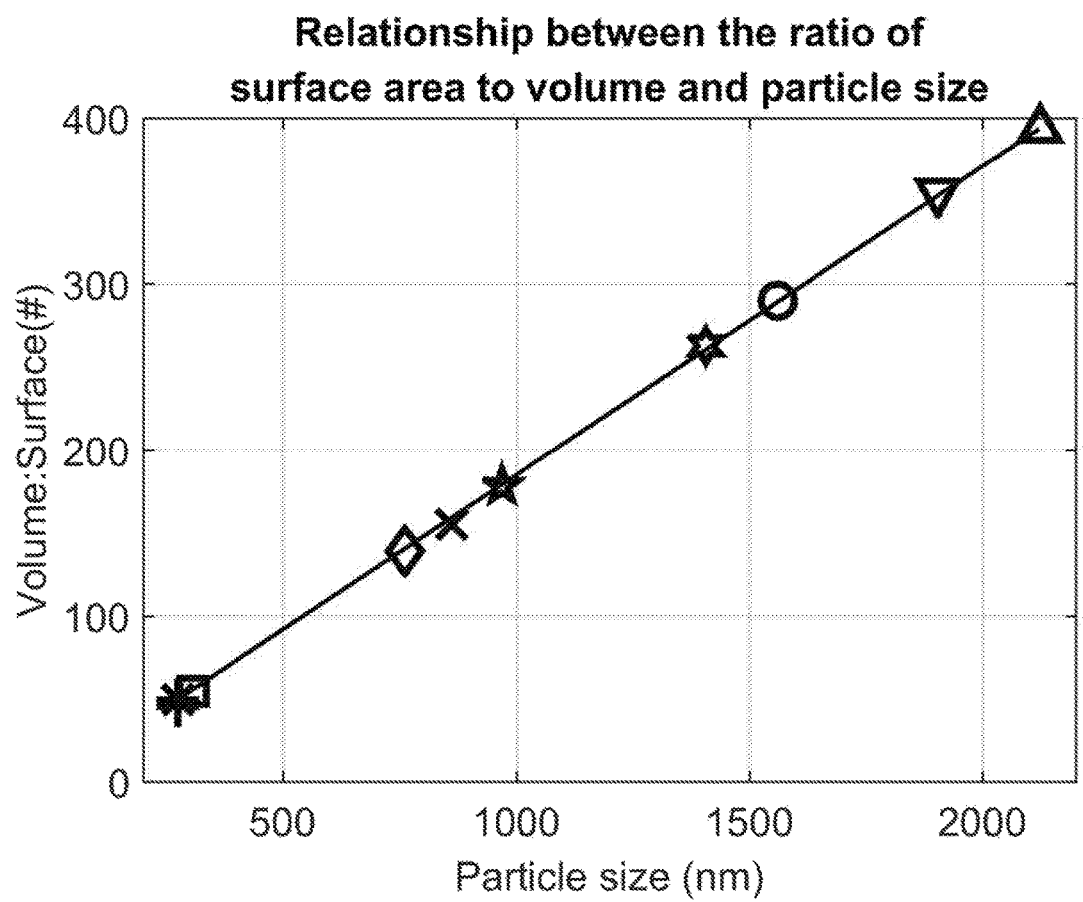

FIG. 7 shows the relationship between the ratio of measured volume concentration to surface area concentration and Sauter diameter. It can be seen that the relationship is completely linear, and non-linear problems with regards to small particle size or large particle size are avoided.

Furthermore, due to the fact that the surface area concentration, the volume or mass concentration and the Sauter mean diameter of the aerosol are directly sensed according to the present embodiment, the present embodiment can also be used as a sensor to be applied to occasions where the characteristic parameters of an aerosol need to be measured in environment monitoring, industrial production and daily life. Any technical schemes formed through equivalent substitution or equivalent conversion fall within the protection scope of the present invention.

Therefore, a fire aerosol and a non-fire aerosol can be distinguished by sensing the three parameters, including surface area concentration, volume (mass) concentration and Sauter mean diameter, of aerosol; and characteristic parameters, including particle size and surface area concentration, of an aerosol can be directly obtained, fire smoke detection accuracy can be improved, and the false alarm rate can be reduced.

The invention claimed is:

1. A method of sensing aerosol characteristic parameters using dual-wavelength light scattered signals, characterized by comprising the following steps:

step 1, constructing a detector consisting of light emitting devices with shorter and longer wavelengths respectively and two channels of detection signals, wherein an included angle between the optical axis of the first channel of light emitting device with shorter wavelength and the optical axis of a light receiving device is larger than 90°, and an included angle between the optical axis of the second channel of light emitting device with longer wavelength and the optical axis of the light receiving device is smaller than 90°;

step 2, for received scattered signal of aerosol by the first channel, expressed by shorter-wavelength light scattered light power $P_S$, calculating the corresponding surface area concentration $C_2$ of the aerosol via the formula below:

$$C_2 = \frac{P_S}{M_2}$$

wherein the unit of $C_2$ is $nm^2/cm^3$, the unit of $P_S$ is voltage V converted from scattered light power, and $M_2$ is a scattered light surface area concentration conversion coefficient which is a constant corresponding to a given optical structure and electric parameters, of which the numerical range is $(1.5\text{-}3.5)\times10^{-10}$, and of which the unit is $V/(nm^2/cm^3)$ when light power is expressed by voltage;

step 3, for received scattered signal of aerosol by the second channel, expressed by longer-wavelength light scattered light power $P_L$, calculating the volume concentration $C_3$ of the aerosol according to the formula below:

$$C_3 = \frac{P_L}{M_3}$$

wherein the unit of $C_3$ is $nm^3/cm^3$, the unit of $P_L$ is voltage V converted from scattered light power, and $M_3$ is a scattered light volume concentration conversion coefficient which is a constant corresponding to a given optical structure and electric parameters, of which the numerical range is $(0.5\text{-}2.5)\times10^{-12}$, and of which the unit is $V/(nm^3/cm^3)$ when light power is expressed by voltage;

step 4, calculating the ratio of the volume concentration $C_3$ of aerosol to the surface area concentration $C_2$ of aerosol according to the formula below, so as to obtain the Sauter mean diameter $D_S$ of aerosol, of which the unit is nm:

$$D_S = 6\frac{C_3}{C_2},$$

and step 5, directly outputting the three parameters, including the volume concentration $C_3$, the surface area concentration $C_2$ and the Sauter diameter $D_S$, of aerosol as aerosol characteristics, and simultaneously comparing the three parameters with corresponding set thresholds $V_{th}$, $S_{th}$ and $D_{th}$:

returning to step 1 when the volume concentration $C_3$ and the surface area concentration $C_2$ are lower than the corresponding preset thresholds $V_{th}$ and $S_{th}$ respectively; and judging whether the particle Sauter mean diameter $D_S$ is larger than the set threshold $D_{th}$ when at least one of the volume concentration $C_3$ and the surface area concentration $C_2$ is higher than the corresponding preset threshold $V_{th}$ or $S_{th}$; if so, emitting a corresponding non-fire factor interference prompt signal; and if not, emitting a corresponding fire alarm signal.

2. The method of sensing aerosol characteristic parameters using the dual-wavelength light scattered signals according to claim 1, characterized in that an ultraviolet light or blue light source with a wavelength of 280-490 nm is adopted to emit shorter-wavelength light, and an infrared light source with a wavelength of 830-1050 nm is adopted to emit longer-wavelength light.

3. The method of sensing aerosol characteristic parameters using the dual-wavelength light scattered signals according to claim 2, characterized in that the included angle between the optical axis of the shorter-wavelength luminescent device and the optical axis of the light receiving device is 110°-130°; and the included angle between the optical axis of the longer-wavelength luminescent device and the optical axis of the light receiving device is 70°-89°.

4. An application of the method of sensing aerosol characteristic parameters using the dual-wavelength light scattered signals according to claim 1 to a fire smoke detection system.

* * * * *